United States Patent [19]
Hattori et al.

[11] Patent Number: 6,008,390
[45] Date of Patent: Dec. 28, 1999

[54] PROCESS FOR PRODUCING N-LONG-CHAIN ACYL ACIDIC AMINO ACIDS OR SALTS THEREOF

[75] Inventors: Tatsuya Hattori; Kiyomiki Hirai, both of Yokkaichi, Japan

[73] Assignee: Ajinomoto Co., Inc., Tokyo, Japan

[21] Appl. No.: 08/927,571

[22] Filed: Sep. 8, 1997

[30] Foreign Application Priority Data

Sep. 6, 1996 [JP] Japan .................................. 8-255303

[51] Int. Cl.⁶ .................................................. C07C 231/00
[52] U.S. Cl. .................... 554/69; 554/68; 554/70; 564/133; 564/142; 564/143; 252/32.5
[58] Field of Search .............................. 252/32.5; 554/68, 554/69, 70; 564/133, 142, 143

[56] References Cited

U.S. PATENT DOCUMENTS

| | | | |
|---|---|---|---|
| 3,945,931 | 3/1976 | Bussi et al. | 252/32.5 |
| 3,985,722 | 10/1976 | Yoshida et al. | |
| 5,334,713 | 8/1994 | Hattori et al. | |
| 5,529,712 | 6/1996 | Sano et al. | |

FOREIGN PATENT DOCUMENTS

| | | |
|---|---|---|
| 24 49 445 | 4/1975 | Germany . |
| 1 483 500 | 8/1977 | United Kingdom . |
| WO 91 12229 | 8/1991 | WIPO . |
| WO 94 27561 | 12/1994 | WIPO . |

OTHER PUBLICATIONS

Fpat abstr. of JP–05004952, Jan. 1993.
Patent Abstracts of Japan, vol. 17, No. 266 (C–1062), May 25, 1993, JP 5–004952, Jan. 14, 1993.
Patent Abstracts of Japan, vol. 95, No. 4, May 31, 1995, JP 7–002747, Jan. 6, 1995.

*Primary Examiner*—Deborah D Carr
*Attorney, Agent, or Firm*—Oblon, Spivak, McClelland, Maier & Neustadt, P.C.

[57] ABSTRACT

N-long-chain acyl acidic amino acids or salts thereof are prepared by condensing an acidic amino acid or a salt thereof and a $C_8$–$C_{22}$ long-chain fatty acid chloride in an aqueous solvent with stirring at a stirring power of not less than 0.2 kW/m³ while keeping the pH in the range of 10–13.

12 Claims, No Drawings

PROCESS FOR PRODUCING N-LONG-CHAIN ACYL ACIDIC AMINO ACIDS OR SALTS THEREOF

BACKGROUND OF THE INVENTION

1. Field of the Invention

The present invention relates to a process for producing N-long-chain acyl acidic amino acids and in particular to a process for producing N-long-chain acyl acidic amino acids by reacting an acidic amino acid, glutamic acid or aspartic acid, or its salt with a long-chain fatty acid chloride.

2. Description of the Background

It is known that inorganic salts such as sodium, potassium salts, and the like, as well as organic salts such as triethanolamine salt, and the like, of N-long-chain acyl acidic amino acids such as N-long-chain acyl glutamic acid or aspartic acid have surface activating action, sterilizing action, and the like, and are thus useful for various purposes such as detergents, dispersants (i.e., dispersing agents), emulsifying agents, anti-fungus agents (i.e., antibacterial agents) and the like.

A method of condensing glutamic acid with a long-chain fatty acid chloride in an aqueous solvent in the presence of an alkali is known as a method of synthesizing N-long-chain acyl acidic amino acids such as N-long-chain acyl glutamic acid (e.g., see Reference Example at the beginning of column 7 of Japanese Published Patent Application Kokai No. 35058/1973). However, this prior art method has the problem that the yield of the desired N-long-chain acyl glutamic acid is low relative to the long-chain fatty acid chloride.

An improvement in the method is capable of producing the desired N-long-chain acyl acidic acid efficiently with improvement in the reaction rate and reaction yield, and the reaction is completed in high yields in a short time. In this method a tertiary amine or quaternary ammonium salt is used as the catalyst (Japanese Published Patent Application Kokai No. 35058/1973 supra). However, in this method, a catalyst should be used and additional problems are encountered such as the requirement for more facilities and additional process steps.

In an alternative method for increasing yield, the reaction is conducted in a mixed solvent of water and an organic solvent such as acetone, methyl ethyl ketone, dioxane, tetrahydrofuran or the like, but the use of these and other such organic solvents presents problems which include the requirement of additional facilities, the influence of such solvents on the working environment and, particularly safety considerations which include meeting fire code regulations and the consequent necessity of investing in facilities to meet fire code regulations.

Therefore, in view of the necessity for improving the working environment which employs organic solvents, thereby demanding vigilence in the safe handling of the solvents and the necessity of providing facilities to prevent the adverse impact of the organic solvents on the environment, a need has continued to exist for a method of producing N-long-chain acyl acidic amino acids in an aqueous solvent system without the use of any organic solvents.

SUMMARY OF THE INVENTION

Accordingly, one object of the present invention is to provide a method of producing N-long-chain acyl acidic amino acids from an acidic amino acid and a long chain fatty acid chloride in the absence of organic solvents in yields as high as possible.

Briefly, this object and other objects of the present invention as hereinafter will become more readily apparent can be attained by a process for producing N-long-chain acyl acidic amino acids or salts thereof by condensing an acidic amino acid or a salt thereof and a $C_8$–$C_{22}$ long-chain fatty acid chloride in an aqueous solvent under stirring at a stirring power of not less than 0.2 kW/m$^3$ while keeping the pH in the range of 10–13.

DETAILED DESCRIPTION OF THE PREFERRED EMBODIMENTS

The acidic amino acid or its salt as one of the starting materials in the present process is glutamic acid, aspartic acid or a salt thereof. These acids can be, but are not particularly limited to the optically active or racemic forms. Suitable examples of acid salts include the alkali metal salts such as the sodium salt, the potassium salt and the like.

The long-chain fatty acid chloride with which the acidic amino acid or its salt is to be reacted includes $C_8$–$C_{22}$ straight chain or branched chain, saturated or unsaturated fatty acid chlorides. The long-chain fatty acid chlorides include single-component fatty acid chlorides such as oleoyl chloride, nonanoyl chloride, undecanoyl chloride, lauroyl chloride, tridecanoyl chloride, myristoyl chloride, stearoyl chloride and palmitoyl chloride. Further, various sorts of mixed fatty acid chlorides such as palm oil fatty acid chloride, tallow fatty acid chloride, hardened tallow fatty acid chloride, soybean oil fatty acid chloride, cottonseed oil fatty acid chloride, and the like can also be similarly used.

The base which maintains alkaline reaction conditions in the range of pH 10–13 is not particularly limited, and examples thereof include sodium hydroxide, potassium hydroxide, calcium hydroxide, sodium carbonate and ammonia, among which sodium hydroxide is particularly preferred.

In the present invention, an acidic amino acid or its salt and a long-chain fatty acid chloride are allowed to react with each other in an aqueous solvent with stirring while the pH is maintained within the range of pH 10–13.

One of the major characterizing features of the present process is that this stirring is carried out under strong stirring conditions at a stirring power of not less than 0.2 kW/m$^3$, preferably not less than 0.3 kW/m$^3$. By selecting such strong stirring conditions for the condensation reaction, a yield as high as 80% or more can be attained for the desired N-long-chain acyl acidic amino acid (see Table 1 below). Even though the same aqueous solvent is used in the Reference Example in Japanese Published Patent Application Kokai No. 35058/1973 above, the yield obtained was only 50 odd percent.

The following formula (1) is known as a formula by which the amount of energy required for the necessary stirring (power (P) consumed for stirring) in a reaction vessel (see pages 505 and 553 in "Kakuhan Gijyutu" (Stirring Technology) edited by Satake Kagaku Kikai Kogyo K.K. and compiled under the supervision of Kazuo Yamamoto et al. (published in 1992 by Satake Kagaku Kikai Kogyo K.K.) is determined.

$$P = NT/97376 \ (kW) \qquad (1)$$

where N is the number of rotations of the stirring shaft (1/min.), and T is the stirring torque (kgf·cm).

According to the present invention, the power consumed for stirring per unit volume of reaction solution is defined as stirring power (Q) as an indicator of the stirring conditions in the reaction vessel, as by formula (2):

$$Q = NT/97376V \ (kW/m^3) \quad (2)$$

wherein V is the volume of reaction solution (m³).

As is evident from the formulas above, stirring power is rendered independent on the volume of a reaction solution in a reaction vessel, and the stirring power can be used as an indicator of stirring conditions, and as an indicator of reaction yields as well.

It is necessary that as the reaction proceeds, the viscosity of the reaction solution remain within a certain allowable range in order to use the stirring power (Q) as an indicator of the reaction yield of the present invention. With respect to this, the change of electric current applied to a rotating blade in a bench-plant scale procedure was determined every 10 minutes over 3 hours and 45 minutes from initiation until the termination of the reaction. The applied electric current was 5.7 A (ampere) just after the initiation of the reaction, and it was 5.5 A at the time of termination of the reaction, and even during the reaction, it was almost constant in the range of 5.2–5.6 A. Even in the actual viscosity measurement of the reaction system by the method of the present invention, the viscosity was 10 cp or thereabout before the reaction, and it was about 50 cp or thereabout after the reaction (as determined at 20° C. with a Brookfield type viscometer), so it is not necessary to take into consideration an increase in stirring torque as a consequence of an increase in viscosity.

The reaction temperature in the present process is not particularly limited, and the condensation reaction proceeds over a wide range of, e.g., about –20° C. to about 50° C. In order to obtain a high yield, e.g., a yield as high as 80% or more, however, the temperature is preferably in the range of –10–30° C., more preferably 5–30° C. A lower temperature within this range will bring about a higher yield of the desired product.

With respect to the ratio of the acidic amino acid or its salt to the long-chain fatty acid chloride, it is preferable to use the former in an at least equimolar amount relative to the latter in order to increase the yield of the desired product, and a higher ratio of the former within this range will bring about a higher yield.

Yield as defined herein is the yield of the N-long-chain acyl acidic amino acid or its salt relative to (i.e., on the basis of) the long-chain fatty acid chloride.

In order to achieve a high yield, e.g., 80% or more, the ratio (molar ratio) of the acidic amino acid or its salt to the long-chain fatty acid chloride should be within the range of 1.1–1.5 for practical purposes.

If the initial concentration of an acidic amino acid or its salt at the start of the reaction is 25% or more, the yield of the desired product will exceed 80%, and a 53% yield will be brought about by an initial concentration of 19%, a 78% yield by 20%, and a 83% yield by 30%. For a high yield of the desired product N-long-chain acyl acidic amino acid or its salt therefore, the initial concentration of an acidic amino acid or its salt is preferably within the range of 20–60%, more preferably 25–50% to achieve a high yield of 80% or more.

After the reaction is completed, if the reaction mixture is made acidic with a mineral acid such as sulfuric acid, hydrochloric acid or the like, crude crystals of the N-long-chain acyl acidic amino acid precipitate. The crude crystals after separated, e.g., by filtering, are washed in the usual manner with an alkane solvent such as petroleum benzine, whereby the N-long-chain acyl acidic amino acid can be obtained in high yields. On the other hand, the separated crude crystals are neutralized with an aqueous NaOH solution, an aqueous KOH solution, an aqueous triethanol amine solution or the like to give the corresponding N-long-chain acyl acidic amino acid salt.

Having now generally described the invention, a further understanding can be obtained by reference to certain specific examples which are provided herein for purposes of illustration only and are not intended to be limiting unless otherwise specified.

EXAMPLE 1

Synthesis of N-lauroyl-L-glutamic acid/laboratory scale (1)

A 5.0 g (0.27 mol) amount of monosodium L-glutamate was suspended in 60 ml water and 41.5 g of aqueous 25% sodium hydroxide solution was added thereto to prepare an aqueous solution with a pH of 12.0. While this solution was kept at 20° C. with stirring at a stirring power of 0.44 kW/m³, 45.0 g (0.20 mol) of lauric acid chloride and 18.8 g of aqueous 25% sodium hydroxide solution were simultaneously added dropwise to the solution over a period of 1 hour during which the pH and temperature were maintained at the values described above. After this dropwise addition was finished, the mixture was stirred for an additional 1.5 hours, and 13.9 g of aqueous 25% sodium hydroxide solution was consumed to complete the reaction.

The reaction mixture was adjusted to pH 1 with 15% sulfuric acid, and cold water was introduced into therein to precipitate crystals. The weight of the crystals separated by centrifugation was 62 g. From the result of analysis by HPLC, it was found that the yield of the N-lauroyl-L-glutamic acid was 83% (based on the lauric acid chloride). In this connection, the HPLC analysis technique makes use of an ODS column and methanol/a pH 3 phosphate buffer (a 75/25 mixture) as an eluent (detection at 210 nm at a temperature of 60° C.)

The same experiment was repeated where the stirring power was varied as shown in Table 1 below. The results (yields) are also shown in the same table. For reference, the number of revolutions is also shown.

EXAMPLE 2

Synthesis of N-lauroyl-L-glutamic acid/laboratory scale (2)

A 50 g (0.27 mol) amount of monosodium L-glutamate was suspended in 60 ml water and 41.5 g of aqueous 25% sodium hydroxide solution was added thereto to prepare an aqueous solution with a pH of 12.0. While this solution was kept at 10° C. with stirring with a homogenizer (stirring power: 25.0 kW/m³), 45.0 g (0.20 mol) of lauric acid chloride and 33.5 g of aqueous 25% sodium hydroxide solution were simultaneously dropped into the solution over a period of 2 hours during which the pH and temperature were maintained at the values described above. After this dropwise addition was finished, the mixture was stirred for an additional 0.5 hour, and 2.1 g of aqueous 25% sodium hydroxide solution was consumed to complete the reaction.

The reaction mixture was adjusted to pH 1 with 15% sulfuric acid and cold water was added to it to precipitate crystals. The weight of the crystals separated by centrifugation was 65 g. The result of analysis of the crystals in the same manner as in Example 1 indicated that the yield of the N-lauroyl-L-glutamic acid was 87%.

EXAMPLE 3

Synthesis of N-cocoyl-L-glutamic acid/commercial plant scale (1)

A 800 kg (4.3 kilomol) amount of monosodium L-glutamate was suspended in 975 L water and 800 kg of aqueous 25% sodium hydroxide solution was added to it to prepare an aqueous solution with a pH of 12.0. While this solution was kept at 20° C. with stirring at a stirring power of 0.61 kW/m$^3$, 783 kg (3.3 kilomol) of cocoyl chloride and 542 kg of aqueous 25% sodium hydroxide solution were simultaneously dropped into the solution over a period of 3 hours during which the pH and temperature were maintained at the values described above. After this dropwise addition was finished, the mixture was stirred for an additional 1.5 hours, and 117 kg of aqueous 25% sodium hydroxide solution was consumed to complete the reaction.

The reaction mixture was adjusted to pH 1 with 15% sulfuric acid and cold water was added thereto to precipitate crystals. The weight of the crystals separated by centrifugation was 975 kg. The result of the analysis of the crystals in the same manner as described in Example 1 indicated that the yield of the N-cocoyl-L-glutamic acid was 80%.

EXAMPLE 4

Synthesis of N-cocoyl-L-glutamic acid/bench plant scale (1)

A 22.6 kg (121 mol) amount of monosodium L-glutamate was suspended in 27.5 L water and 18.9 kg of aqueous 25% sodium hydroxide solution was added thereto to prepare an aqueous solution with a pH of 12.0. While this solution was kept at 20° C. with stirring at a stirring power of 0.70 kW/m$^3$, 20.8 kg (93 mol) of cocoyl chloride and 15.3 kg of aqueous 25% sodium hydroxide solution were simultaneously dropped into the solution over a period of 2 hours during which the pH and temperature were maintained at the values described above. After this dropwise addition was finished, the mixture was stirred for an additional 1.0 hour, and 3.3 kg of aqueous 25% sodium hydroxide solution was consumed to complete the reaction.

The reaction mixture was adjusted to pH 1 with 15% sulfuric acid and cold water was added thereto to precipitate crystals. The weight of the crystals separated by centrifugation was 29 kg. The result of the analysis of the crystals in the same manner as described in Example 1 indicated that the yield of the N-cocoyl-L-glutamic acid was 83%.

The results of Examples 1–4 are collectively shown in Table 1 below. In this table, Experiment Nos. L1a to L1c refer to Comparative Examples.

TABLE 1

Relationship Between Stirring Power and Yield

| Experiment Number | Stirring Power (kW/m$^3$) | Yield (%) | Revolution Number (rpm) |
| --- | --- | --- | --- |
| L1a | 0.003 | 33 | 50 |
| L1b | 0.03 | 40 | 100 |
| L1c | 0.09 | 51 | 150 |
| L1d | 0.22 | 75 | 200 |
| L1e | 0.30 | 81 | 220 |
| L1f | 0.44 | 83 | 250 |
| CP | 0.61 | 80 | 105 |
| L1g | 0.63 | 83 | 270 |
| BP | 0.70 | 83 | 277 |

TABLE 1-continued

Relationship Between Stirring Power and Yield

| Experiment Number | Stirring Power (kW/m$^3$) | Yield (%) | Revolution Number (rpm) |
| --- | --- | --- | --- |
| L1h | 0.71 | 82 | 300 |
| L1i | 0.91 | 83 | 350 |
| L1j | 1.00 | 84 | 360 |
| L1k | 1.47 | 84 | 400 |
| L1l | 2.71 | 84 | 500 |
| L1m | 3.29 | 84 | 550 |
| L2 | 25.0 | 87 | 20,000 |

L1a−L1m: Laboratory scale (1)
L2: Laboratory scale (2)
CP: Commercial Plant scale (1)
BP: Bench plant scale (1)

L1a−L1m: Laboratory scale (1)
L2: Laboratory scale (2)
CP: Commercial Plant scale (1)
BP: Bench plant scale (1)

EXAMPLE 5

Synthesis of N-cocoyl-L-aspartic acid

A 50 g (0.38 mol) amount of L-aspartic acid was suspended in 45 ml water and 118 g of aqueous 25% sodium hydroxide solution was added thereto to prepare an aqueous solution with a pH of 12.0. While this solution was kept at 20° C. with stirring at a stirring power of 0.48 kW/m$^3$, 64.6 g (0.29 mol) of cocoyl chloride and 33 g of aqueous 25% sodium hydroxide solution were simultaneously dropped into the solution over a period of 3 hours during which the pH and temperature were maintained at the values described above. After this dropwise addition was finished, the mixture was stirred for an additional 1.5 hours, and 22 g of aqueous 25% sodium hydroxide solution was consumed to complete the reaction.

The reaction mixture was adjusted to pH 1 with 15% sulfuric acid and cold water was added thereto to precipitate crystals. The crystals were recovered by filtration, and the result of the analysis of the crystals by HPLC indicated that N-cocoyl-L-aspartic acid was obtained in an 80% yield.

Effects of the Invention

According to the present invention, N-long-chain acyl acidic acids or salts thereof, which are useful in facial washing agents, hair and body cleaning agents etc., can be easily obtained in high yields by reacting a long-chain fatty acid chloride with acidic amino acid or its salt in an aqueous solution.

The disclosure of Japanese priority Application No. 255,303/96 filed Sep. 6, 1996 is hereby incorporated by reference.

Obviously, numerous modifications and variations of the present invention are possible in light of the above teachings. It is, therefore, to be understood that within the scope of the appended claims, the invention may be practiced otherwise than as specifically described herein.

What is claimed as new and desired to be secured by Letters Patent of the United States is:

1. A process for producing N-long-chain acyl acidic amino acids or salts thereof, which comprises:

condensing an acidic amino acid or a salt thereof and a $C_8$–$C_{22}$ long-chain fatty acid chloride in an aqueous solvent with no organic solvent present with stirring at a stirring power of not less than 0.2 kW/m$^3$ while keeping the pH in the range of 10–13.

2. The process of claim 1, wherein said stirring power is not less than 0.3 kW/m$^3$.

3. The process of claim 1, wherein the condensation reaction is conducted at a temperature of about −20° C. to about 50° C.

4. The process of claim 3, wherein the temperature ranges from −10 to 30° C.

5. The process of claim 4, wherein the temperature ranges from 5–30° C.

6. The process of claim 1, wherein said long-chain fatty acid chloride is oleoyl chloride, nonanoyl chloride, undecanoyl chloride, lauroyl chloride, tridecanoyl chloride, myristoyl chloride, stearoyl chloride or palmitoyl chloride.

7. The process of claim 1, wherein said long-chain fatty acid chloride is a mixed fatty acid chloride is a member selected from the group consisting of palm oil fatty acid chloride, tallow fatty acid chloride, hardened fatty acid chloride, soybean oil fatty acid chloride and cottonseed fatty acid chloride.

8. The process of claim 1, wherein the reaction mixture is acidified to precipitate crude crystals of N-long-chain acylacidic amino acid.

9. The process of claim 8, wherein the acid for the acidification is sulfuric acid or hydrochloric acid.

10. The process of claim 9, wherein the precipitated crystals are separated.

11. The process of claim 9, wherein the separated crystals are washed with alkane solvent.

12. A process for producing N-long-chain acyl acidic amino acids or salts thereof, which comprises:

condensing an acidic amino acid or a salt thereof and a $C_8$–$C_{22}$ long-chain fatty acid chloride in an aqueous solvent with no organic solvent present with stirring at a stirring power of not less than 0.2 kW/m$^3$ and a temperature of about −20° C. to about 50° C. while keeping the pH in the range of 10–13.

* * * * *

UNITED STATES PATENT AND TRADEMARK OFFICE
CERTIFICATE OF CORRECTION

PATENT NO. : 6,008,390

DATED : December 28, 1999

INVENTOR(S): Tatsuya HATTORI et al.

It is certified that an error appears in the above-identified patent and that said Letters Patent is hereby corrected as shown below:

Column 6, line 52, after "with" insert --an--.

Column 7, line 18, delete "is a member".

Signed and Sealed this

Tenth Day of April, 2001

Attest:

NICHOLAS P. GODICI

*Attesting Officer*     *Acting Director of the United States Patent and Trademark Office*